United States Patent [19]
Gilbeau

[11] Patent Number: 6,063,941
[45] Date of Patent: May 16, 2000

[54] PROCESS FOR THE REGENERATION OF CATALYSTS

[75] Inventor: Patrick Gilbeau, Braine-le-Comte, Belgium

[73] Assignee: Solvay (Societe Anonyme), Belgium

[21] Appl. No.: 09/294,364

[22] Filed: Apr. 20, 1999

Related U.S. Application Data

[63] Continuation of application No. PCT/EP97/05688, Oct. 9, 1997.

[30] Foreign Application Priority Data

Oct. 25, 1996 [BE] Belgium ................ 09600912

[51] Int. Cl.$^7$ .................................................. C07D 301/02
[52] U.S. Cl. .................................................. 549/518
[58] Field of Search ............................... 549/518

[56] References Cited

U.S. PATENT DOCUMENTS

| | | | |
|---|---|---|---|
| 5,258,555 | 11/1993 | Pinkos et al. | 568/835 |
| 5,354,875 | 10/1994 | Nemeth et al. | 549/531 |

FOREIGN PATENT DOCUMENTS

| | | |
|---|---|---|
| 2195574 | 1/1996 | Canada . |
| 0 100 119 | 2/1984 | European Pat. Off. . |
| 0 200 260 A2 | 12/1986 | European Pat. Off. . |
| 0 267 362 A1 | 5/1988 | European Pat. Off. . |
| 0 376 453 | 7/1990 | European Pat. Off. . |
| 0 538 729 A2 | 4/1993 | European Pat. Off. . |
| 0 631 983 A1 | 1/1995 | European Pat. Off. . |
| 44 25 672 A1 | 1/1996 | Germany . |
| 44 35 239 A1 | 4/1996 | Germany . |
| 3-114536 | 5/1991 | Japan . |

OTHER PUBLICATIONS

Grasselli, R.K. and Sleight, A.W. (Editors), *Structure–Activity and Selectivity Relationships in Heterogeneous Catalysis* (1991) Elsevier Science Publishers B.V., Amsterdam, pp. 243–255: Notari, "Titanium Silicate: A New Selective Oxidation Catalyst".

Applied Catalysis A:General 92 (1992) Elsevier Science Publishers B.V., Amsterdam, pp. 93–111: Van Der Pol et al., "Parameters affecting the synthesis of titanium silicate 1".

*Primary Examiner*—Amelia Owens
*Attorney, Agent, or Firm*—Larson & Taylor

[57] ABSTRACT

The invention relates to a process for the regeneration of a catalyst of titanium silicalite type used in particular in reactions for the oxidation of saturated hydrocarbons or for the epoxidation of olefins by treatment with a liquid solution containing an oxidizing agent.

14 Claims, No Drawings

PROCESS FOR THE REGENERATION OF CATALYSTS

This application is a continuation of PCT/EP97/05688 Oct. 9, 1997.

FIELD OF THE INVENTION

The subject of the present invention is a process for the regeneration of catalysts of titanium silicalite type, catalysts which are used in particular in reactions between hydrogen peroxide and an organic coreactant.

BACKGROUND OF THE INVENTION

It is known to use a titanium silicalite as catalyst, in particular in oxidation reactions of saturated hydrocarbons to form alcohols or ketones, as described in European Patent Application EP-A-376,453, or in epoxidation reactions of olefins, as described in Patent Application EP-A-100,119, or alternatively in hydroxylation reactions of aromatic compounds, as reported in Application EP-A-200,260.

However, the activity of these catalysts rapidly falls. It consequently seems essential to have available a means for regenerating them in order to be able to use them repeatedly.

Patent Application JP 03/114536 describes a process for the regeneration of catalysts of titanium silicalite type by washing with methanol, ketones or benzene. However, it is not possible with this regeneration process to rapidly and completely recover the initial catalytic activity of the catalyst.

SUMMARY OF THE INVENTION

The aim of the present invention is to provide a process for the regeneration of catalysts of titanium silicalite type which is more efficient than the known process.

The invention consequently relates to a process for the regeneration of a catalyst of titanium silicalite type, comprising a treatment of the spent catalyst with a liquid solution, which is characterized in that the liquid solution comprises at least one oxidizing agent chosen from hydrogen peroxide, ozone and organic peroxide compounds. Examples of organic peroxides which can be used in the process according to the invention are performic acid, peracetic acid and perfluoroperacetic acid. Hydrogen peroxide is preferred.

DETAILED DESCRIPTION OF THE PREFERRED EMBODIMENTS

The catalysts of titanium silicalite type to which the regeneration process according to the invention is applied are synthetic crystalline materials with a structure analogous to that of zeolites, comprising titanium and silicon oxides and characterized by an infrared absorption band at approximately 950–960 cm$^{-1}$. Their general formula is typically:

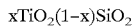

$$xTiO_2(1-x)SiO_2$$

in which x is between 0.0001 and 0.5, preferably between 0.001 and 0.05.

Materials of this type, known under the name of TS-1, exhibit a microporous crystalline zeolitic structure analogous to that of zeolite ZSM-5. The properties and the main applications of these compounds are known (B. Notari; Structure-Activity and Selectivity Relationship in Heterogeneous Catalysis; R. K. Grasselli and A. W. Sleight Editors; Elsevier; 1991; p. 243–256). Their synthesis has been studied in particular by A. Van der Poel and J. Van Hooff (Applied Catalysis A; 1992; Volume 92, pages 93–111). Other materials of this type have a structure analogous to that of beta-zeolite or of zeolite ZSM-11.

The liquid regeneration solution can be composed essentially of the oxidizing agent. In an alternative form, it can additionally comprise an additive or a solvent for the oxidizing agent, that is to say a compound with which the oxidizing agent is completely miscible. Should the occasion arise, the said additive or solvent must be inert with respect to the oxidizing agent under the conditions of the regeneration. A polar solvent, such as a halogenated solvent, for example trichloromethane, or water is highly suitable as solvent for the oxidizing agent. Water is particularly advantageous. When the spent catalyst has been used in a reaction involving hydrogen peroxide and an organic coreactant, the regeneration treatment is generally carried out in the substantial absence of the organic coreactant.

The liquid solution generally does not contain more than 90% by weight of oxidizing agent. Preferably, a solution not containing more than 50% by weight of oxidizing agent is used. In a particularly preferred way, a solution not containing more than 20% by weight of oxidizing agent is used. Generally, the liquid solution contains at least 0.5% by weight of oxidizing agent. Advantageously, it contains at least 1% thereof.

A very particularly preferred solution in the process according to the invention is an aqueous hydrogen peroxide solution assaying from 1 to 10% by weight of hydrogen peroxide, preferably from 2 to 5% by weight of hydrogen peroxide.

The catalyst can be treated with the liquid regeneration solution by any appropriate means, for example by immersion of the catalyst in the liquid solution when the catalyst is in the form of dispersed particles or by passing the said solution through the bed of the catalyst when the catalyst is employed as a stationary bed. Generally, from 0.25 to 50 liters of liquid solution are used per kilo of catalyst to be treated. Preferably, from 0.5 to 10 liters thereof are used per kilo of catalyst.

The oxidizing agent can be introduced continuously or non-continuously (by successive introductions of several doses of oxidizing agent) during the treatment or by introduction of a single dose of oxidizing agent at the beginning of the treatment.

It is preferable to carry out the treatment continuously or non-continuously with successive introductions. This makes it possible, on the one hand, to keep the concentration of oxidizing agent constant and, on the other hand, to limit the risk of decomposition of the oxidizing agent which would be difficult to control. In addition, this makes it possible to avoid explosive phenomena.

The catalyst is generally treated with the liquid solution at a temperature between ambient temperature and the boiling temperature of the solution. A regeneration temperature of at least 50° C. and not exceeding 100° C. is preferred. Treatment with an aqueous hydrogen peroxide solution at a temperature in the region of approximately 90° C. has given excellent results.

The pressure at which the process according to the invention is carried out is not critical in itself, provided that it is sufficient to keep the solution essentially in the liquid form.

The treatment time is variable according to the state of deactivation of the catalyst. It is generally between 10 minutes and a few hours. Excellent results have been obtained with a treatment time not exceeding 2 hours.

The process for regenerating the catalyst advantageously comprises washing the catalyst prior to the treatment with the liquid solution containing the oxidizing agent, in order to remove substantially all the compounds with which the catalyst was in contact in the reaction in which it was employed. Washing consists in bringing the catalyst into contact with water or with an organic compound. Organic compounds are preferred. This is because the latter make it possible to avoid the formation of two separate phases. In addition, they exhibit a high solubility for the organic compounds responsible for the deactivation of the catalysts. The organic compounds can be chosen from aliphatic, cyclic, aromatic or alcoholic organic diluents. They preferably contain up to 20 carbon atoms. Alcohols are well suited. Methanol is particularly preferred. It can prove to be advantageous to use, for washing, the diluent employed during the use of the catalyst.

The washing temperature is generally from 25° C. to the boiling temperature of the organic washing compound. This washing is carried out by bringing the catalyst into contact with water or with the organic compound for a period of 5 minutes to 2 hours. Preferably, the washing stage does not exceed 30 minutes. In a particularly advantageous way, washing comprises a first stage of washing with an organic compound and a second stage of washing with water.

The process according to the invention makes it possible to restore virtually all the initial activity of the catalyst by a treatment of short duration.

It can be advantageous to control the pH during the treatment. This is because this makes it possible to prevent corrosion of the equipment used for the treatment. In addition, this makes it possible, when the catalyst is dispersed in a binder, to prevent attack on this binder by the acids released during the treatment. Controlling the pH also makes it possible to limit the decomposition of the oxidizing agent by metals released during the treatment. Generally, the pH is maintained at a value of at least 2, in particular of at least 4. The pH usually does not exceed 8, preferably 7. This is because alkaline pH values can affect the activity of the catalyst. The treatment is preferably carried out at a pH maintained in the range from 2 to 8, more particularly from 4 to 7. The pH can be controlled by addition of alkali, for example of sodium hydroxide.

The process according to the invention applies to spent catalysts of titanium silicalite type, in particular those used in a reaction employing hydrogen peroxide and an organic coreactant, in particular those used in reactions for the epoxidation of olefins, for the hydroxylation of aromatic compounds or for the oxidation of saturated hydrocarbons. It applies more particularly to catalysts used in reactions for the epoxidation of olefins by means of hydrogen peroxide. It applies very particularly to catalysts used in the reaction for the epoxidation of allyl chloride to epichlorohydrin. In addition, the process can be applied to catalysts used in the reaction for the epoxidation of propylene to propylene oxide by means of hydrogen peroxide.

When catalysts for the epoxidation of olefins are involved, it can be interesting to recycle a liquid effluent arising from the preparation of the epoxide and to reuse this effluent for the regeneration of the catalyst. This is particularly interesting when the epoxidation and the regeneration are carried out using the same oxidising agent, for instance hydrogen peroxide. The effluent arising from the preparation of the epoxide can already contain the oxidising agent, i.e. the part which has not been consumed during epoxidation. A quantity of oxidising agent can also be added to the effluent.

The invention is consequently also related to a process for the synthesis of epoxides by reaction between an olefin and hydrogen peroxide in the presence of a catalyst regenerated according to the above described regeneration process, in which a liquid effluent arising from the epoxide synthesis is recycled and used for the regeneration of the catalyst.

The invention is illustrated more fully in the following non-limiting examples.

EXAMPLE 1

9.5 grams of catalyst of titanium silicalite type TS-1 were placed in a 125 ml reactor equipped with a recirculation loop (total volume=250 ml). The reactor was fed continuously at a flow rate of 250 ml/hour with a solution of allyl chloride and of hydrogen peroxide in methanol (allyl chloride/ $H_2O_2$=2 mol/mol; $H_2O_2$ concentration of 1.38 mol/kg) at a temperature of 25° C. The linear rate of passage of the solution recirculating through the reactor was adjusted to 1 m/min. The hydrogen peroxide concentration in the reaction mixture withdrawn was measured by iodometry. As soon as the degree of conversion of the hydrogen peroxide was 25% less than that obtained after operating for one hour, the reactor was emptied. The catalyst was washed with 250 ml of methanol circulating through the reactor in a loop system at a flow rate of 30 l/hour at a temperature of 65° C. for 10 minutes. After emptying the methanol, the catalyst was washed in an analogous way with water at 75° C. The water was discharged and then the catalyst was treated in an analogous way with a 3.5% by weight aqueous hydrogen peroxide solution at 85° C. for 1 hour. The aqueous solution was emptied and the reactor was again fed with the solution of allyl chloride and of hydrogen peroxide in methanol under the conditions set out above.

11 cycles, the same as that described above, of use/ regeneration of the catalyst were carried out. At each cycle, the activity of the regenerated catalyst was measured by determining the amount of epichlorohydrin produced under these conditions before the degree of conversion of the hydrogen peroxide again fell by 25% with respect to its initial value measured after operating for one hour. A constant activity of 127 grams of epichlorohydrin was observed during each of the 11 cycles.

EXAMPLE 2

Example 1 was repeated but using a liquid solution containing 1.06% of hydrogen peroxide at a temperature of 86° C. The epichlorohydrin yield was 117 grams.

EXAMPLE 3 (comparison)

Example 1 was repeated but using, as liquid solution, water not containing hydrogen peroxide at 85° C. for 1 hour. The epichlorohydrin yield was 90 grams.

What is claimed is:

1. A method of synthesis of epoxides by reaction between an olefin and hydrogen peroxide, said reaction employing regenerated titanium silicalite catalyst, the catalyst being regenerated by a process which comprises treating a spent titanium silicalite catalyst with a liquid solution comprising at least one oxidizing agent chosen from hydrogen peroxide, ozone and organic peroxide compounds, and maintaining the pH of the solution in the range from 4 to 7.

2. A method according to claim 1, in which the catalyst has been used in a reaction employing hydrogen peroxide and an organic coreactant which is an olefin, an aromatic compound or a saturated hydrocarbon.

3. A method according to claim 2, in which said treatment is carried out in the absence of said organic coreactant.

4. A method according to claim 1, in which the oxidizing agent comprises hydrogen peroxide.

5. A method according to claim 1, in which said liquid solution comprises an aqueous solution containing from 1 to 10% by weight of hydrogen peroxide.

6. A method according to claim 1, in which said treatment is carried out at a temperature between ambient temperature and the boiling temperature of said solution.

7. A method according to claim 1, in which said treatment does not last more than 2 hours.

8. A method according to claim 1, in which, prior to said treatment, the catalyst is submitted to washing.

9. A method according to claim 8, in which said washing is carried out by means of an organic compound.

10. A method according to claim 9, in which said organic compound comprises methanol.

11. A method according to claim 1, in which the oxidizing agent is supplied by continuous introduction or by non-continuous introduction of successive doses.

12. A method according to claim 1 of synthesis of epichlorohydrin by reaction between allyl chloride and hydrogen peroxide.

13. A method according to claim 1 of synthesis of propylene oxide by reaction between propylene and hydrogen peroxide.

14. A method according to claim 1, in which, said solution comprises a liquid effluent arising from epoxide synthesis, said effluent being recycled and used to regenerate the catalyst.

* * * * *